(12) United States Patent
Mori et al.

(10) Patent No.: US 6,723,869 B1
(45) Date of Patent: Apr. 20, 2004

(54) METHOD FOR PRODUCING ACRYLONITRILE, CATALYST FOR USE THEREIN AND METHOD FOR PREPARING THE SAME

(75) Inventors: Kunio Mori, Yokohama (JP); Yutaka Sasaki, Kamakura (JP); Kenichi Miyaki, Yokohama (JP); Hirokazu Watanabe, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 110 days.

(21) Appl. No.: 10/110,129

(22) PCT Filed: Oct. 17, 2000

(86) PCT No.: PCT/JP00/07193

§ 371 (c)(1),
(2), (4) Date: Apr. 9, 2002

(87) PCT Pub. No.: WO01/28985

PCT Pub. Date: Apr. 26, 2001

(30) Foreign Application Priority Data

Oct. 18, 1999 (JP) ............................. 11/295913

(51) Int. Cl.$^7$ .................. C07C 253/26; B01J 23/78

(52) U.S. Cl. .................. 558/324; 502/205; 502/212

(58) Field of Search .................. 558/324; 502/205, 502/212

(56) References Cited

U.S. PATENT DOCUMENTS 5,134,105 A * 7/1992 Paparizos et al. ........... 502/205

FOREIGN PATENT DOCUMENTS

| EP | 404529 | 12/1990 |
| EP | 475351 | 3/1992 |
| EP | 476579 | 3/1992 |
| JP | 11-246504 | 9/1999 |

* cited by examiner

Primary Examiner—Joseph K. McKane
Assistant Examiner—Kamal Saeed
(74) Attorney, Agent, or Firm—Oblon, Spivak, McClelland, Maier & Neustadt, P.C.

(57) ABSTRACT

For the production of acrylonitrile by ammoxidation of propylene, there is provided a catalyst capable of giving a high yield for a long period of time. In producing acrylonitrile by ammoxidation of propylene, there is used a metal oxide as a catalyst, which metal oxide contains iron, antimony, molybdenum, bismuth, potassium, an F element, a G element, an H element and silica as essential components in a specific composition ratio, and in which metal oxide iron antimonate exists as a crystal phase, provided that the F element is at least one element selected from the group consisting of magnesium, calcium, strontium, barium, manganese, cobalt, nickel, copper, silver, zinc and cadmium, the G element is at least one element selected from the group consisting of chromium, aluminum, gallium and indium, and the H element is at least one element selected from the group consisting of yttrium, lanthanum, cerium, praseodymium, neodymium and samarium.

7 Claims, No Drawings

METHOD FOR PRODUCING ACRYLONITRILE, CATALYST FOR USE THEREIN AND METHOD FOR PREPARING THE SAME

TECHNICAL FIELD

The present invention relates to a catalyst suitably used for the production of acrylonitrile by ammoxidation of propylene, a process for producing said catalyst and a process for producing acrylonitrile by using said catalyst.

BACKGROUND ART

With respect to the production of acrylonitrile by ammoxidation of propylene, various catalysts suitably used therefor are disclosed. In JP-B-38-17967, there is disclosed an oxide catalyst containing molybdenum, bismuth and iron, and in JP-B-38-19111, there is disclosed an oxide catalyst containing iron and antimony. After that, studies have been extensively continued to improve these catalysts. For example, in JP-B-51-33888, JP-B-55-56839, JP-B-58-2232, JP-B-61-26419, JP-A-7-47272, JP-A-10-43595, JP-A-4-11805 and the like, there are disclosed one improvement comprising using another component in addition to molybdenum, bismuth and iron, and the other improvement comprising using another component in addition to iron and antimony.

Further, in using these catalysts for the ammoxidation reaction, it is proposed to carry out the reaction while supplying a molybdenum-containing material thereto in the ammoxidation reaction, thereby maintaining the catalyst efficiency. For example, in JP-B-58-57422, there is disclosed a process, wherein a particle formed by supporting a molybdenum-containing material on silica is supplied to a fluidized bed catalyst containing molybdenum, bismuth, iron, cobalt and others, thereby restoring the catalyst efficiency. In DE 3,311,521 C2 and WO 97/33863, there is disclosed a process, wherein molybdenum trioxide or a molybdenum compound capable of converting to said trioxide in a specific amount is supplied to a catalyst similar to that mentioned above. Also with respect to a catalyst containing iron and antimony, there is known a similar proposal, for example, in JP-B-2-56938 and JP-B-2-56939.

These catalysts of the prior arts are effective to improve a yield of acrylonitrile to a certain extent. However, further improvements of these catalysts have been requested. Particularly, these catalysts have not been sufficient in respect to repeatability in the production thereof, their structural stability and long-term stability of the yield of desired products. Also with respect to a catalyst containing iron and antimony, particularly a molybdenum component-enriched catalyst containing a crystal phase of iron antimonate, which is disclosed in JP-A-4-118051, it has been very important to improve those from an industrial point of view and therefore further investigation of these catalysts have been required. In addition, also with respect to the process comprising supplying the molybdenum component to maintain the catalyst efficiency, it is difficult to say that it is always effective. Even if the molybdenum-containing material is supplied, no effect can be observed in the case where a catalyst structure is markedly damaged. Further, even if loss of molybdenum is not so large, no effect can be exhibited in the case where lowering of the catalyst efficiency is mainly caused by change of the catalyst structure. It is finding that the catalyst to be applied itself should be stable and should have no extreme damage on its structure.

It has been desired to find a catalyst, which satisfies requisites such as further improvement of the yield of the desired acrylonitrile, superior long-term stability when used for the ammoxidation reaction, and long-term maintenance of its efficiency by the supply of a molybdenum-containing material. An object of the present invention is to solve these problems and particularly to improve the catalyst composition disclosed in JP-A-4-118051, thereby giving a catalyst more suitably used for the production of acrylonitrile by fluidized bed ammoxidation reaction. Another object of the present invention is also to improve the reaction processes disclosed in JP-B-2-56938 and JP-B-2-56939.

DISCLOSURE OF INVENTION

The present inventors have undertaken extensive studies to solve the above-mentioned problems. As a result, they found that a catalyst containing elements such as iron, antimony, molybdenum, bismuth and potassium etc. and iron antimonate within a limited composition region can exhibit a superior catalyst efficiency, and that the efficiency can be maintained for a longer period of time by carrying out the ammoxidation reaction while appropriately adding a molybdenum-containing material thereto.

The present catalyst composition is capable of giving a high acrylonitrile yield and stable in a catalyst structure. Still, in the case where such a catalyst is used for the ammoxidation reaction without interruption, a decrease of the acrylonitrile yield, which appears mainly due to escaping of the molybdenum component, may be observed. Since the ammoxidation reaction is carried out at a temperature exceeding 400° C., it seems that the escaping of the molybdenum component at the time of reaction is inevitable in this kind of catalyst having a large molybdenum content. In this regard, the acrylonitrile yield was able to be maintained at a higher degree for a longer period of time by continuing the reaction while adding and supplying the molybdenum-containing material. According to the catalyst in accordance with the present invention, which is structurally stable, the yield of desired products can be more sufficiently restored by adding the molybdenum-containing material at the time of the ammoxidation reaction. Moreover, since the addition of the molybdenum-containing material at the time of the ammoxidation reaction can be repeated, the catalyst in accordance with the present invention can be used for a much longer period of time by such a repeated addition of the molybdenum-containing material.

The addition of the molybdenum-containing material may be carried out from an early stage of the reaction. In applying the catalyst to the ammoxidation reaction, it is general that a catalyst surface composition and a catalyst structure are optimized by means of a composition, a preparation method or the like. However, it is difficult to say that the optimization can be always realized. As the case may be, the yield of the desired product increases by addition of the molybdenum-containing material at the start of the reaction. This seems that the optimization of the catalyst surface composition and the structure thereof can be realized also with the aid of the molybdenum-containing material.

With respect to a conventional catalyst, the acrylonitrile yield has been insufficient as mentioned above, and it has been also insufficient to restore the catalyst efficiency even if the molybdenum-containing material is added on the grounds that the yield decreases owing to a long-term use. However, according to the present invention, there is provided a process capable of maintaining a high acrylonitrile yield for a long period of time.

That is, the present invention provides a process for producing acrylonitrile, which comprises using a fluidized bed catalyst of a composition represented by the following empirical formula in the production of acrylonitrile by ammoxidation of propylene. The present invention also provides a process for producing acrylonitrile according said process, wherein the ammoxidation reaction is carried out while supplying a molybdenum-containing material. Further, the present invention provides said fluidized bed catalyst and a process for producing said fluidized bed catalyst.

$$Fe_a\ Sb_b\ Mo_c\ Bi_d\ K_e\ F_f\ G_g\ H_h\ Q_q\ R_r\ T_t\ O_x\ (SiO_2)_y$$

In the formula, Fe, Sb, Mo, Bi and K are iron, antimony, molybdenum, bismuth and potassium, respectively; F is at least one element selected from the group consisting of magnesium, calcium, strontium, barium, manganese, cobalt, nickel, copper, silver, zinc and cadmium; G is at least one element selected from the group consisting of chromium, aluminum, gallium and indium; H is at least one element selected from the group consisting of yttrium, lanthanum, cerium, praseodymium, neodymium and samarium; Q is at least one element selected from the group consisting of titanium, zirconium, vanadium, niobium, tantalum, tungsten, germanium, tin and lead; R is at least one element selected from the group consisting of lithium, sodium, rubidium, cesium and thallium; T is at least one element selected from the group consisting of boron, phosphorus and tellurium; O is oxygen; Si is silicon; and affixes a, b, c, d, e, f, g, h, q, r, t, x and y are independently of one another an atomic ratio, provided that a is a number larger than 0, and when a=10, then b=5 to 60, preferably 6 to 30, more preferably 6.5 to 20, c=5 to 50, preferably 8 to 45, more preferably 10 to 40, d=0.15 to 5, preferably 0.2 to 3, more preferably 0.3 to 2.5, e=0.1 to 5, preferably 0.2 to 3, more preferably 0.3 to 1, f=2 to 35, preferably 3 to 30, more preferably 6 to 24, g=0.05 to 10, preferably 0.1 to 8, more preferably 0.3 to 4, h=0.05 to 10, preferably 0.1 to 8, more preferably 0.3 to 4, h/c is larger than 0.02, preferably 0.025 to 1, more preferably 0.03 to 0.5, q=0 to 10, preferably 0 to 8, more preferably 0 to 4, r=0 to 5, preferably 0 to 4, more preferably 0 to 2, t=0 to 5, preferably 0 to 4, more preferably 0 to 2, x is a number of oxygen in a metal oxide formed by bonding of said respective components, and y=20 to 500, preferably 25 to 200, more preferably 30 to 180; and in which iron antimonate exists as a crystal phase.

Embodiments of the present invention are explained in more detail as follows.

It is essential that the fluidized bed catalyst in accordance with the present invention contains iron, antimony, molybdenum, bismuth, potassium, the F component element, the G component, the H component and silica (SiO$_2$) as essential components, and further contains iron antimonate as a crystal phase. If these components are not used in the above-defined composition range, the objects of the present invention cannot be accomplished.

The iron antimonate is a compound represented by a chemical formula, FeSbO$_4$, which is disclosed in the above-mentioned JP-A-4-118051 and JP-A-10-231125, and the existence thereof can be confirmed by an X-ray diffraction of the catalyst. The iron antimonate is essential for improving an acrylonitrile yield and for qualification of physical properties of the catalyst. Bismuth is essential to afford a catalyst capable of increasing the acrylonitrile yield with high stability, and it is finding that there is a preferred composition region for that purpose. When potassium is too little, it may happen that by-products increase, thereby decreasing the acrylonitrile yield. Whereas, when it is too large, it may happen that the reaction rate decreases, thereby decreasing the acrylonitrile yield.

The F, G and H components serve for stabilization of the catalyst structure. When their amounts to be added are too small, the catalyst tends to become structurally unstable, and so there is a tendency that it becomes difficult to maintain a satisfactory acrylonitrile yield for a long period of time. When the amounts are too large, there is a tendency that the acrylonitrile yield decreases. As the F component, preferred is at least one element selected from the group consisting of magnesium, calcium, manganese, cobalt, nickel and zinc, and more preferred is a component containing at least nickel. As the G component, preferred is a component containing at least chromium. As the H component, preferred is at least one element selected from the group consisting of lanthanum, cerium, praseodymium, neodymium and samarium, and more preferred is a component containing at least cerium.

As the catalyst components, the above-mentioned Q, R and T components may be further incorporated. As the case may be, these can be added for the purpose of stabilization of the catalyst structure, improvement of oxidation reduction characteristics, control of acidity and basicity and others. As the Q component, preferred are zirconium, vanadium, niobium, tungsten and germanium. As the R component, preferred are sodium, rubidium and cesium, and particularly preferred are rubidium and cesium. If desired, the T component may be incorporated in a small amount for the purpose of improving the acrylonitrile selectivity, controlling the by-products or others.

The process for producing acrylonitrile in accordance with the present invention is carried out according to a fluidized bed reaction. Accordingly, the catalyst is additionally required to have physical properties suitable for the fluidized bed reaction. That is, it is additionally required that its bulk density, particle strength, attrition resistance, specific surface area, fluidity and others are suitable. For that purpose, silica is used as a carrier component.

For preparing the catalyst in accordance with the present invention, it is permitted to apply a process appropriately selected from those disclosed in the above-mentioned prior arts.

For preparing iron antimonate, various processes are proposed. For example, there are processes disclosed in JP-A-4-118051 and JP-A-10-231125, and a process to be applied may be selected therefrom. In the production of the catalyst in accordance with the present invention, it is important that iron antimonate is prepared in advance according to these processes, for example a process described in JP-A-10-231125, and thereafter is mixed with other catalyst component materials. The iron antimonate prepared may contain a small amount of an element other than antimony and iron. The existing iron antimonate serves for the improvement of acrylonitrile selectivity and physical properties of the fluidized bed catalyst.

Materials used for the molybdenum component include molybdenum oxide and ammonium paramolybdate, wherein ammonium paramolybdate is preferably used. Materials used for the bismuth component include bismuth oxide, bismuth nitrate, bismuth carbonate and bismuth oxalate, wherein bismuth nitrate is preferably used. Materials used for the iron components include iron nitrate such as ferrous nitrate (iron (II) nitrate) and ferric nitrate (iron (III) nitrate), and iron oxalate such as ferrous oxalate (iron (II) oxalate) and ferric oxalate (iron (III) oxalate), wherein preferred is the iron nitrate. Materials used for the potassium component include potassium nitrate and potassium hydroxide, wherein potassium nitrate is preferably used. Materials of the F, G and R components include respective oxides, hydroxides and nitrates, wherein preferred are nitrates, and materials of the H and Q components include respective oxides, hydroxides, nitrates, oxygen acids and their salts, wherein preferred are nitrates, oxygen acids and their salts. With respect to the T component, materials used for boron include boric acid and anhydrous boric acid, wherein anhydrous boric acid is preferably used, materials used for phosphorus include phosphoric acid such as orthophosphoric acid, and materials used for tellurium include metal tellurium, tellurium dioxide, tellurium trioxide and telluric acid. Materials used for silica include silica sol and fumed silica. It is convenient to use silica sol.

The iron antimonate can be blended with materials of other components to obtain a slurry. These catalyst materials are blended, and thereafter the resulting mixture is subjected to spray drying and calcination to obtain a desired fluidized bed catalyst. The catalyst materials are blended and, if necessary pH of the slurry was adjusted, and the resulting slurry is subjected to heat treatment and others thereby to be able to prepare a catalyst slurry. In preparing the catalyst slurry, preparation conditions such as a mixing means of the materials, temperature, pressure and atmosphere can be voluntarily determined. When the slurry is prepared by adjusting pH of the slurry to a relatively high degree such as 3 to 8, it is recommendable to add a chelating agent such as ethylenediamine tetraacetate, lactic acid, citric acid, tartaric acid and gluconic acid according to a process disclosed in Japanese Patent No. 2747920, thereby preventing the slurry from gelling. In the case where the pH is adjusted to a relatively low degree such as 1 to 3 to prepare it, it is not always necessary to add the chelating agent. However, when added in a small amount, good results may be obtained.

The thus prepared slurry can be dried by means of spray drying. A spray drying apparatus is not particularly limited, and may be a conventional one such as a rotary-disk type and a nozzle type. A slurry concentration of the slurry entering the spray drying apparatus is preferably from about 10 to about 40% by weight in terms of an oxide of the element constituting the catalyst. The catalyst materials can be granulated by means of the spray drying. A spray drying temperature is not particularly limited. In carrying out the spray drying, pressure and atmosphere can be voluntarily determined. These spray-drying conditions are determined so as to obtain a catalyst having a desired particle diameter as a fluidized bed catalyst.

After completion of the drying, calcination can be carried out to obtain a desired fluidized bed catalyst. In carrying out the calcination, calcination conditions such as a calcination means, temperature, pressure and atmosphere can be voluntarily determined. For example, the calcination can be carried out at 200 to 500° C., and additionally at 500 to 700° C. for 0.1 to 20 hours. A calcination atmosphere is preferably an oxygen containing gas. It is conveniently carried out in air, which may be used in combination with a combination of oxygen and nitrogen, carbonic acid gas, water vapor or the like. For the calcination, a box type calciner, a tunnel type calciner, a rotary calciner, a fluidized bed calciner and others can be used.

It is recommendable to adjust a particle diameter of the thus obtained fluidized bed catalyst to preferably from 5 to 200 μm, more preferably from 20 to 150 μm. Incidentally, the particle diameter used herein is not an average particle diameter of the whole particles, but a particle diameter of the individual particles.

In using the molybdenum containing fluidized bed catalyst for the production of an unsaturated nitrile, as mentioned above, it is known that the molybdenum-containing material is added during the reaction, thereby maintaining the yield of the desired product. However, such an effect cannot be expected to a sufficient extent unless such a process is applied to a catalyst having a stable catalyst structure. Since the catalyst in accordance with the present invention is structurally stable even when used for a long period of time at a temperature exceeding 400° C., at which this kind of the ammoxidation reaction is carried out, the reaction can be continued while adding the molybdenum-containing material, thereby maintaining the yield of desired products equal or superior to those of the early stage. However, even when such a structurally stable catalyst is used, the molybdenum component evaporates little by little from the catalyst under a reaction condition, and maybe this causes damage of the catalyst structure. Accordingly, when the molybdenum-containing material is supplied, it is necessary that the molybdenum-containing material be supplied before it becomes impossible to restore such a damage of the catalyst structure.

The molybdenum-containing material used here includes metal molybdenum, molybdenum trioxide, molybdic acid, ammonium dimolybdate, ammonium paramolybdate, ammonium octamolybdate, ammonium dodecamolybdate, phosphomolybdic acid, and those obtained by supporting these molybdenum-containing materials with an inert substance or the above-mentioned catalyst. Of these, preferred are molybdenum trioxide, ammonium paramolybdate and those obtained by supporting these molybdenum-containing materials with an inert substance or the above-mentioned catalyst. Although the molybdenum-containing material can be used in a gaseous state or a liquid state, it is preferred from a practical point of view that these solid molybdenum-containing materials are used in a powder state. It is particularly effective to apply a process comprising using a molybdenum-enriched catalyst obtained by enriching the above-mentioned catalyst with the molybdenum-containing material. According to the process, molybdenum in the molybdenum-containing material added can be efficiently utilized, and troubles caused by precipitation of the molybdenum oxide in the system or other reasons can be avoided. For preparing the molybdenum-enriched catalyst, the process described in JP-A-11-33400 or the like can be applied.

These molybdenum-containing materials may be added in a reactor in a continuous or intermittent manner at intervals. The time of addition and an amount to be added may be appropriately determined in consideration of a relation between the yield of desired products and operation facility. The amount added at a time is preferably from 0.01 to 3% by weight, more preferably from 0.05 to 2% by weight, as molybdenum element based on the weight of the catalyst filled in a reactor. It is necessary to pay attention to the followings. When the molybdenum-containing material is added in a large amount in a time, it may happen that the substance wastefully escapes out of the reaction system, thereby resulting in useless consumption, and moreover the material precipitates or accumulates inside of the reactor or adheres to a heat exchanger, thereby causing operational problems. When it is added in an intermittent manner, a total amount of the molybdenum-containing material added may be within the range as mentioned above.

The ammoxidation of propylene is usually carried out at a reaction temperature of 370 to 500° C. under a reaction pressure of from atmospheric pressure to 500 kPa using a feeding gas having a composition of propylene/ammonia/ oxygen=1/0.9 to 1.3/1.6 to 2.5 (molar ratio). An apparent contact time is usually from 0.1 to 20 seconds. It is convenient to use air as an oxygen source, which air may be diluted with water vapor, nitrogen, carbonic acid gas, a saturated hydrocarbon or the like, or may be enriched with oxygen.

BEST MODE FOR CARRYING OUT INVENTION

The present invention is explained in more detail with reference to Examples and Comparative Examples, which are not intended to limit the scope of the present invention.

Determination of Catalyst Activity

Synthesis of acrylonitrile by means of ammoxidation of propylene was carried out as follows to evaluate the catalyst activity.

A catalyst was filled in a fluidized bed reactor having a catalyst fluidizing zone of an inner diameter of 25 mm and a height of 400 mm, and a mixed gas having a composition of propylene/ammonia/air/water vapor=1/1.2/9.5/0.5 (molar ratio) was introduced therein at a linear velocity of the gaseous feedstock of 4.5 cm/sec. The reaction pressure was controlled to 200 kPa.

Still, at the time of reaction, a molybdenum-containing material was appropriately added. The molybdenum-containing material such as some molybdenum compounds and molybdenum component-enriched catalysts was added, at intervals of 100 to 500 hours, in an amount of 0.1 to 0.2% by weight as molybdenum element based on the weight of the catalyst filled in a reactor. The molybdenum-containing material, which was in a powder state, was fed from an upper part of the reactor.

Contact time and the acrylonitrile yield were found according to the following calculation equations, respectively.

Contact time (sec)=Volume of catalyst (ml) based on apparent bulk density/Flow rate of feeding gas converted to reaction conditions (ml/sec)

Acrylonitrile yield (%)=Mole number of acrylonitrile produced/Mole number of propylene supplied x100

EXAMPLE 1

A catalyst of a composition, $Fe_{10}$ $Sb_{9.2}$ $Mo_{15}$ $Bi_{0.6}$ $K_{0.3}$ $Co_{2.25}$ $Ni_6$ $Cr_{1.2}$ $Ce_{0.6}$ $P_{0.3}$ $B_{0.3}$ $O_x$ $(SiO_2)_{55}$ (x is a number naturally determined depending upon the valence numbers of the other elements), was prepared as follows.

In 3000 g of pure water, 304.9 g of ammonium paramolybdate was dissolved, and successively 2.9 g of 85% phosphoric acid and 1.2 g of anhydrous boric acid were added thereto. The resulting liquid was mixed with another liquid obtained by dissolving 33.5 g of bismuth nitrate, 3.5 g of potassium nitrate, 75.4 g of cobalt nitrate, 200.9 g of nickel nitrate, 55.3 g of chromium nitrate, 30 g of cerium nitrate and 24.9 g of citric acid in 270 g of 3.3% nitric acid. A liquid obtained by dissolving 76.8 g of ferric nitrate and 25 g of citric acid in 270 g of pure water was prepared and added thereto. Successively, 1902.5 g of 20% silica sol was added thereto. The resulting slurry was adjusted to pH 2 by addition of 15% aqueous ammonia while being stirred, and subjected to heat treatment at 98° C. for 1.5 hours. Further, 1198.5 g of a 20% iron antimonate slurry separately prepared was added thereto.

The thus prepared slurry was spray-dried using a rotary disk type spray drier, whose inlet temperature and outlet temperature were controlled to 330° C. and 160° C., respectively. The dried particle was subjected to heat treatment at 250° C. for 2 hours and additionally at 400° C. for 2 hours, and finally subjected to fluidized calcination at 670° C. for 3 hours.

Incidentally, the iron antimonate slurry used was prepared as follows.

To a mixture of 1815 g of 65% by weight nitric acid and 1006 g of pure water, 218 g of electrolytic iron powder was added little by little. After the iron powder was completely dissolved, 629 g of antimony trioxide powder was added thereto, and then 10% aqueous ammonia was dropwise added thereto to adjust the pH to 1.8 while being stirred. The resulting slurry was heated at 98° C. for 3 hours under stirring. The slurry was dried using a spray drier, whose inlet temperature and outlet temperature were controlled to 330° C. and 160° C., respectively, and the dried product was subjected to calcination at 250° C. for 2 hours and additionally at 400° C. for 2 hours, and further subjected to calcination at 850° C. for 3 hours under nitrogen atmosphere. After completion of calcination, the product was pulverized, followed by mixing with pure water, thereby obtaining the 20% iron antimonate slurry. In the following Examples and Comparative Examples also, the iron antimonate slurry prepared in such a manner was used.

EXAMPLE 2

A catalyst having a composition of $Fe_{10}$ $Sb_{9.2}$ $Mo_{15}$ $Bi_{0.6}$ $K_{0.3}$ $Ni_{8.25}$ $Cr_{0.75}$ $Ga_{0.45}$ $Ce_{0.6}$ $P_{0.3}$ $O_x$ $(SiO_2)_{55}$ was prepared in a manner similar to that of Example 1, and then subjected to calcination under conditions as shown in Table 1, except that anhydrous boric acid and cobalt nitrate were not added and gallium nitrate as a Ga material additionally dissolved in the above-mentioned nitric acid was added.

EXAMPLE 3

A catalyst having a composition of $Fe_{10}$ $Sb_{8.6}$ $Mo_{20}$ $Bi_{0.8}$ $K_{0.4}$ $Ni_8$ $Ca_{0.6}$ $Zn_{0.4}$ $Cr_{2.4}$ $Al_{0.2}$ $In_{0.2}$ $La_{0.2}$ $Ce_{0.6}$ $Ge_{0.4}$ $B_{0.4}$ $O_x$ $(SiO_2)_{70}$ was prepared in a manner similar to that of Example 1, and then subjected to calcination under conditions as shown in Table 1, except that phosphoric acid and cobalt nitrate were not added, and calcium nitrate, zinc nitrate, aluminum nitrate, lanthanum nitrate and indium nitrate as Ca, Zn, Al, La and In materials, respectively, additionally dissolved in the above-mentioned nitric acid, and germanium oxide as a Ge material were independently added next to the addition of ammonium paramolybdate.

EXAMPLE 4

A catalyst having a composition of $Fe_{10}$ $Sb_{8.0}$ $Mo_{25}$ $Bi_{1.25}$ $K_{0.75}$ $Ni_{12.5}$ $Mg_{2.5}$ $Cr_1$ $Ce_1$ $Pr_{0.25}$ $O_x$ $(SiO_2)_{100}$ was prepared in a manner similar to that of Example 1, and then subjected to calcination under conditions as shown in Table 1, except that phosphoric acid, anhydrous boric acid and cobalt nitrate were not added, and magnesium nitrate and praseodymium nitrate as Mg and Pr materials, respectively, additionally dissolved in the above-mentioned nitric acid were added.

EXAMPLE 5

A catalyst having a composition of $Fe_{10}$ $Sb_{6.9}$ $Mo_{25}$ $Bi_{1.25}$ $K_{0.5}$ $Ni_{12.5}$ $Cr_{1.75}$ $Ce_{1.25}$ $Rb_{0.25}$ $P_{0.25}$ $B_{0.25}$ $O_x$ $(SiO_2)_{90}$ was prepared as follows.

In 3000 g of pure water, 352.8 g of ammonium paramolybdate was dissolved, and successively 1.65 g of 85% phosphoric acid and 0.7 g of anhydrous boric acid were added thereto. The resulting liquid was mixed with another liquid obtained by dissolving 48.5 g of bismuth nitrate, 4.0 g of potassium nitrate, 290.5 g of nickel nitrate, 56.0 g of chromium nitrate, 43.4 g of cerium nitrate, 2.9 g of rubidium nitrate and 25 g of citric acid in 270 g of 3.3% nitric acid. Successively, 2161.1 g of 20% silica sol was added thereto. The resulting mixture was adjusted to pH 7.7 by dropwise-addition of 15% aqueous ammonia while being stirred, and subjected to heat treatment at 98° C. for 1.5 hours. A liquid prepared by dissolving 121.1 g of ferric nitrate and 25 g of citric acid in 270 g of pure water was prepared and added thereto, and further, 623.5 g of a 20% iron antimonate slurry separately prepared was added thereto.

The thus prepared slurry was spray-dried using a rotary disk type spray drier, whose inlet temperature and outlet temperature were controlled to 330° C. and 160° C., respectively. The dried particle was subjected to heat treatment at 250° C. for 2 hours and additionally at 400° C. for 2 hours, and finally subjected to fluidized calcination at 680° C. for 3 hours.

EXAMPLE 6

A catalyst having a composition of $Fe_{10}$ $Sb_{7.7}$ $Mo_{30}$ $Bi_{1.2}$ $K_{0.9}$ $Ni_{16.5}$ $Cr_{1.2}$ $Ce_{2.4}$ $W_{1.5}$ $P_{0.6}$ $O_x$ $(SiO_2)_{110}$ was prepared as follows.

In 3000 g of pure water, 25.5 g of ammonium paratungstate was dissolved, thereafter 344.8 g of ammonium paramolybdate was dissolved therein, and successively 3.29 g of 85% phosphoric acid was added thereto. The resulting liquid was mixed with another liquid obtained by dissolving 37.9 g of bismuth nitrate, 5.9 g of potassium nitrate, 312.4 g of nickel nitrate, 31.3 g of chromium nitrate, 67.8 g of cerium nitrate and 25 g of citric acid in 270 g of 3.3% nitric acid. Successively, 2151.7 g of 20% silica sol was added thereto. The resulting slurry was adjusted to pH 5 by dropwise-addition of 15% aqueous ammonia while being stirred, and subjected to heat treatment under reflux at 98° C. for 1.5 hours. A liquid obtained by dissolving 78.9 g of ferric nitrate and 25 g of citric acid in 270 g of pure water was added thereto, and further, 567.5 g of a 20% iron antimonate slurry separately prepared was added thereto.

The thus prepared slurry was spray-dried using a rotary disk type spray drier, whose inlet temperature and outlet temperature were controlled to 330° C. and 160° C., respectively. The dried particle was subjected to heat treatment at 250° C. for 2 hours and additionally at 400° C. for 2 hours, and finally subjected to fluidized calcination at 690° C. for 3 hours.

EXAMPLE 7

A catalyst having a composition of $Fe_{10}$ $Sb_{6.5}$ $Mo_{30}$ $Bi_{1.2}$ $K_{0.6}$ $Mg_3$ $Ni_{10.5}$ $Mn_{1.5}$ $Cr_{1.2}$ $Ce_{1.2}$ $Nb_{0.3}$ $O_x$ $(SiO_2)_{150}$ was prepared in a manner similar to that of Example 6, and then subjected to calcination under conditions as shown in Table 1, except that ammonium paratungstate and phosphoric acid were not added, and manganese nitrate and magnesium nitrate as Mn and Mg materials, respectively, additionally dissolved in the above-mentioned nitric acid, and niobium hydrogen oxalate as an Nb material were independently added next to the addition of ammonium paramolybdate.

EXAMPLE 8

A catalyst having a composition of $Fe_{10}$ $Sb_{7.4}$ $Mo_{30}$ $Bi_{1.5}$ $K_{0.6}$ $Co_3$ $Ni_{13.5}$ $Cr_{2.4}$ $Ce_{2.1}$ $Cs_{0.3}$ $P_{0.3}$ $O_x$ $(SiO_2)_{120}$ was prepared in a manner similar to that of Example 6, and then subjected to calcination under conditions as shown in Table 1, except that no ammonium paratungstate was added, and cesium nitrate and cobalt nitrate as a Ce material and a Co material, respectively, additionally dissolved in the above-mentioned nitric acid were added.

EXAMPLE 9

A catalyst having a composition of $Fe_{10}$ $Sb_{7.2}$ $Mo_{35}$ $Bi_{1.4}$ $K_{1.05}$ $Ni_{21}$ $Cr_{2.45}$ $Ce_{1.4}$ $Nd_{0.35}$ $Zr_{0.7}$ $P_{0.7}$ $O_x$ $(SiO_2)_{125}$ was prepared in a manner similar to that of Example 6, and then subjected to calcination under conditions as shown in Table 1, except that no ammonium paratungstate was added, and neodymium nitrate and zirconium oxynitrate as an Nd material and a Zr material, respectively, additionally dissolved in the above-mentioned nitric acid were added.

EXAMPLE 10

A catalyst having a composition of $Fe_{10}$ $Sb_{7.5}$ $Mo_{40}$ $Bi_2$ $K_1$ $Ni_{24}$ $Cr_{2.8}$ $Ce_{1.6}$ $Sm_{0.4}$ $V_{0.4}$ $Te_{0.8}$ $O_x$ $(SiO_2)_{140}$ was prepared in a manner similar to that of Example 6, and then subjected to calcination under conditions as shown in Table 1, except that ammonium paratungstate and phosphoric acid were not added, and samarium nitrate as an Sm material additionally dissolved in the above-mentioned nitric acid, and ammonium methavanadate as a V material were independently added next to the addition of ammonium paramolybdate, and moreover a liquid obtained by dissolving telluric acid as a Te material in water was added to the solution of ferric nitrate and citric acid.

COMPARATIVE EXAMPLE 1

A catalyst having a composition of $Fe_{10}$ $Sb_{9.2}$ $Mo_{15}$ $Bi_{0.6}$ $K_{0.3}$ $Ni_{8.25}$ $P_{0.3}$ $O_x$ $(SiO_2)_{55}$ was prepared in a manner similar to that of Example 1, and then subjected to calcination under conditions as shown in Table 1, except that anhydrous boric acid, cobalt nitrate, chromium nitrate and cerium nitrate were not added.

COMPARATIVE EXAMPLE 2

A catalyst having a composition of $Fe_{10}$ $Sb_{9.2}$ $Mo_{15}$ $Bi_{0.6}$ $K_{0.3}$ $Ni_{8.25}$ $La_{0.3}$ $Ce_{0.6}$ $P_{0.3}$ $O_x$ $(SiO_2)_{55}$ was prepared in a manner similar to that of Example 1, and then subjected to calcination under conditions as shown in Table 1, except that anhydrous boric acid, cobalt nitrate and chromium nitrate were not added, and lanthanum nitrate as a La material additionally dissolved in the above-mentioned nitric acid was added.

COMPARATIVE EXAMPLE 3

A catalyst having a composition of $Fe_{10}$ $Sb_{7.4}$ $Mo_{30}$ $Bi_{1.5}$ $K_{0.6}$ $Co_3$ $Ni_{13.5}$ $Cr_{2.4}$ $P_{0.3}$ $O_x$ $(SiO_2)_{110}$ was prepared in a manner similar to that of Example 6, and then subjected to calcination under conditions as shown in Table 1, except that ammonium paratungstate and cerium nitrate were not added, and cobalt nitrate as a Co material additionally dissolved in the above-mentioned nitric acid was added.

COMPARATIVE EXAMPLE 4

A catalyst having a composition of $Fe_{10}$ $Sb_{7.4}$ $Mo_{30}$ $Bi_{1.5}$ $K_{0.6}$ $Co_3$ $Ni_{13.5}$ $Cr_{2.4}$ $Ce_{0.3}$ $P_{0.3}$ $O_x$ $(SiO_2)_{110}$ was prepared in a manner similar to that of Example 6, and then subjected to calcination under conditions as shown in Table 1, except that no ammonium paratungstate was added, and cobalt nitrate as a Co material additionally dissolved in the above-mentioned nitric acid was added.

Incidentally, the molybdenum-enriched catalysts used for the ammoxidation reaction in Examples 3 and 7 to 10 and Comparative Examples 3 and 4 were those prepared by impregnating the catalysts obtained in the corresponding Examples and Comparative Examples with an aqueous solution of ammonium paramolybdate, followed by drying and calcination.

Using the catalysts obtained in these Examples and Comparative Examples, the ammoxidation reaction of propylene was carried out under the above-mentioned conditions. The results were as shown in the following Table.

TABLE 1

| | Catalyst composition (atomic ratio) | | | | | | | | | | | | | | | | | |
|---|---|---|---|---|---|---|---|---|---|---|---|---|---|---|---|---|---|---|
| | Fe | Sb | Mo | Bi | K | F | | | G | | H | Q | R | | T | | SiO$_2$ | h/c |
| Example | | | | | | | | | | | | | | | | | | |
| 1 | 10 | 9.2 | 15 | 0.6 | 0.3 | Ni 6 | Co 2.25 | Cr 1.2 | | | Ce 0.6 | | | | P 0.3 | B 0.3 | 55 | 0.04 |
| 2 | 10 | 9.2 | 15 | 0.6 | 0.3 | Ni 8.25 | | Cr 0.75 | Ga 0.45 | | Ce 0.6 | | | | P 0.3 | | 55 | 0.04 |
| 3 | 10 | 8.6 | 20 | 0.8 | 0.4 | Ni 8 Zn 0.4 | Ca 0.6 | Cr 2.4 | Al 0.2 | In 0.2 | Ce 0.6 | La 0.2 | Ge 0.4 | | B 0.4 | | 70 | 0.04 |
| 4 | 10 | 8.0 | 25 | 1.25 | 0.75 | Ni 12.5 | Mg 2.5 | Cr 1 | | | Ce 1.0 | Pr 0.25 | | | | | 100 | 0.05 |
| 5 | 10 | 6.9 | 25 | 1.25 | 0.5 | Ni 12.5 | | Cr 1.75 | | | Ce 1.25 | | | Rb 0.25 | P 0.25 | B 0.25 | 90 | 0.05 |
| 6 | 10 | 7.7 | 30 | 1.2 | 0.9 | Ni 16.5 | | Cr 1.2 | | | Ce 2.4 | | W 1.5 | | P 0.6 | | 110 | 0.08 |
| 7 | 10 | 6.5 | 30 | 1.2 | 0.6 | Ni 10.5 Mn 1.5 | Mg 3 | Cr 1.2 | | | Ce 1.2 | | Nb 0.3 | | | | 150 | 0.04 |
| 8 | 10 | 7.4 | 30 | 1.5 | 0.6 | Ni 13.5 | Co 3 | Cr 2.4 | | | Ce 2.1 | | | Cs 0.3 | P 0.3 | | 120 | 0.07 |
| 9 | 10 | 7.2 | 35 | 1.4 | 1.05 | Ni 21 | | Cr 2.45 | | | Ce 1.4 | Nd 0.35 | Zr 0.7 | | P 0.7 | | 125 | 0.05 |
| 10 | 10 | 7.5 | 40 | 2 | 1 | Ni 24 | | Cr 2.8 | | | Ce 1.6 | Sm 0.4 | V 0.4 | | Te 0.8 | | 140 | 0.05 |
| Comparative Example | | | | | | | | | | | | | | | | | | |
| 1 | 10 | 9.2 | 15 | 0.6 | 0.3 | Ni 8.25 | | | | | | | | | P 0.3 | | 55 | 0 |
| 2 | 10 | 9.2 | 15 | 0.6 | 0.3 | Ni 8.25 | | | | | Ce 0.6 | La 0.3 | | | P 0.3 | | 55 | 0.06 |
| 3 | 10 | 7.4 | 30 | 1.5 | 0.6 | Ni 13.5 | Co 3 | Cr 2.4 | | | | | | | P 0.3 | | 110 | 0 |
| 4 | 10 | 7.4 | 30 | 1.5 | 0.6 | Ni 13.5 | Co 3 | Cr 2.4 | | | Ce 0.3 | | | | P 0.3 | | 110 | 0.01 |

| | Calcination conditions | | Reaction conditions | | Acrylonitrile yield [%] | | | | |
|---|---|---|---|---|---|---|---|---|---|
| | Temperature [° C.] | Time [hr] | Temperature [° C.] | Contact time [sec] | Time elapsed [hr] | | | Kind of Molybdenum added | |
| | | | | | 50 | 500 | 1000 | | |
| Example | | | | | | | | | |
| 1 | 670 | 3 | 440 | 3.0 | 82.0 | 81.9 | 82.1 | Ammonium paramolybdate | |
| 2 | 650 | 3 | 440 | 2.8 | 82.1 | 82.0 | 81.9 | Molybdenum trioxide | |
| 3 | 660 | 3 | 440 | 2.9 | 81.4 | 81.5 | 81.3 | Molybdenum-enriched catalyst | |
| 4 | 680 | 3 | 440 | 3.2 | 81.7 | 81.4 | 81.5 | Molybdenum trioxide | |
| 5 | 680 | 3 | 440 | 2.5 | 81.0 | 81.2 | 80.9 | Ammonium paramolybdate | |
| 6 | 690 | 3 | 440 | 3.4 | 81.4 | 81.2 | 81.1 | " | |
| 7 | 650 | 3 | 440 | 2.9 | 81.3 | 81.5 | 81.3 | Molybdenum-enriched catalyst | |
| 8 | 640 | 3 | 440 | 3.1 | 80.8 | 80.7 | 80.5 | " | |
| 9 | 630 | 3 | 440 | 3.3 | 81.3 | 81.2 | 81.2 | " | |
| 10 | 660 | 3 | 440 | 2.3 | 81.7 | 81.8 | 81.4 | " | |
| Comparative Example | | | | | | | | | |
| 1 | 640 | 3 | 440 | 2.1 | 81.8 | 80.5 | 79.0 | Ammonium paramolybdate | |
| 2 | 630 | 3 | 440 | 2.3 | 81.5 | 80.9 | 79.3 | " | |
| 3 | 660 | 3 | 440 | 3.4 | 81.1 | 80.2 | 78.9 | Molybdenum-enriched catalyst | |
| 4 | 670 | 3 | 440 | 3.5 | 81.3 | 80.3 | 78.8 | " | |

INDUSTRIAL APPLICABILITY

The process for producing acrylonitrile in accordance with the present invention can give a high acrylonitrile yield. Moreover, it is possible to increase long-term stability of the reaction owing to a stable catalyst structure, and to maintain the catalyst efficiency for a long period of time by adding and supplying a molybdenum component.

What is claimed is:

1. A process for producing acrylonitrile, which comprises using a fluidized bed catalyst of a composition represented by the following empirical formula in the production of acrylonitrile by ammoxidation of propylene, $$Fe_a Sb_b Mo_c Bi_d K_e F_f G_g H_h Q_q R_r T_t O_x (SiO2)_y$$

wherein Fe, Sb, Mo, Bi and K are iron, antimony, molybdenum, bismuth and potassium, respectively; F is at least one element selected from the group consisting of magnesium, calcium, strontium, barium, manganese, cobalt, nickel, copper, silver, zinc and cadmium; G is at least one element selected from the group consisting of chromium, aluminum, gallium and indium; H is at least one element selected from the group consisting of yttrium, lanthanum, cerium, praseodymium, neodymium and samarium; Q is at least one element selected from the group consisting of titanium, zirconium, vanadium, niobium, tantalum, tungsten, germanium, tin and lead; R is at least one element selected from the group consisting of lithium, sodium, rubidium, cesium and thallium; T is at least one element selected from the group consisting of boron, phosphorus and tellurium; O is oxygen; Si is silicon; and affixes a, b, c, d, e, f, g, h, q, r, t, x and y are independently of one another an atomic ratio, provided that a is a number larger than 0, and when a=10, then b=5 to 60, c=5 to 50, d=0.15 to 5, e=0.1 to 5, f=2 to 35, g=0.05 to 10, h=0.05 to 10, h/c is larger than 0.02, q=0 to 10, r=0 to 5, t=0 to 5, x is a number of oxygen in a metal oxide formed by bonding of said respective components, and y=20 to 500; and in which iron antimonate exists as a crystal phase.

2. The process for producing acrylonitrile according to claim 1, wherein the ammoxidation reaction is carried out while adding a molybdenum-containing material.

3. The process for producing acrylonitrile according to claim 2, wherein the molybdenum-containing material to be added is a molybdenum-enriched catalyst obtained by enriching said fluidized bed catalyst with molybdenum.

4. The process according to claim 1, wherein F is a at least one element selected form the group consisting of magnesium, calcium, manganese, cobalt, nickel and zinc; G contains at least chromium; H is at least one element selected from the group consisting of lanthanum, cerium, praseodymium, neodymium and samarium; Q is at least one element selected from the group consisting of zirconium, vanadium, niobium, tungsten and germanium; R is at least one element selected from the group consisting of sodium, rubidium and cesium; and when a=10, then b=6 to 30, c=8 to 45, d=0.2 to 3, e=0.2 to 3, f=3 to 30, g=0.1 to 8, h=0.1 to 8, h/c=0.025 to 1, q=0 to 4, t=0 to 4, and y=25 to 200.

5. The process according to claim 2, wherein the molybdenum-containing material is added in an amount of from 0.05 to 2% by weight as molybdenum element based on the weight of said fluidized bed catalyst.

6. The process according to claim 3, wherein the molybdenum-containing material is added in an amount of from 0.05 to 2% by weight as molybdenum element based on the weight of said fluidized bed catalyst.

7. The process according to claim 4, wherein the molybdenum-containing material is added in an amount of from 0.05 to 2% by weight as molybdenum element based on the weight of said fluidized bed catalyst.

* * * * *